United States Patent [19]

Morris

[11] 4,117,839

[45] Oct. 3, 1978

[54] INTRAUTERINE DEVICE

[76] Inventor: John McLean Morris, Cedar Rd., Woodbridge, Conn. 06525

[21] Appl. No.: 797,369

[22] Filed: May 16, 1977

Related U.S. Application Data

[62] Division of Ser. No. 549,584, Feb. 13, 1975, Pat. No. 4,038,978.

[51] Int. Cl.² ............................................. A61F 5/46
[52] U.S. Cl. ................................................... 128/130
[58] Field of Search ............................... 128/127–131, 128/260

[56] References Cited

U.S. PATENT DOCUMENTS

| 3,507,274 | 4/1970 | Soichet | 128/130 |
|---|---|---|---|
| 3,645,258 | 2/1972 | Massouros | 128/130 |
| 3,678,927 | 7/1972 | Soichet | 128/130 |
| 3,683,906 | 8/1972 | Robinson | 128/130 |
| 3,734,090 | 5/1973 | Shubeck | 128/130 |
| 3,811,435 | 5/1974 | Soichet | 128/130 |
| 3,913,572 | 10/1975 | Wheeler | 128/130 |

Primary Examiner—Lawrence W. Trapp
Attorney, Agent, or Firm—DeLio and Montgomery

[57] ABSTRACT

An intrauterine device providing a membrane to cover substantially the entire surface of the uterine cavity, said device having a Y- and or V-shaped resilient member with two diverging arms, a membrane covering the entire area between the diverging arms and, in addition, extending above an imaginary line passing through the terminal ends of the arms, and a flexible tail or string connected to the intersection of the arms for aiding in the removal of the device from the uterus when desired. Optionally, the arms may having a plurality of flexible spurs extending therefrom for maintaining the intrauterine device in position within the uterus.

5 Claims, 3 Drawing Figures

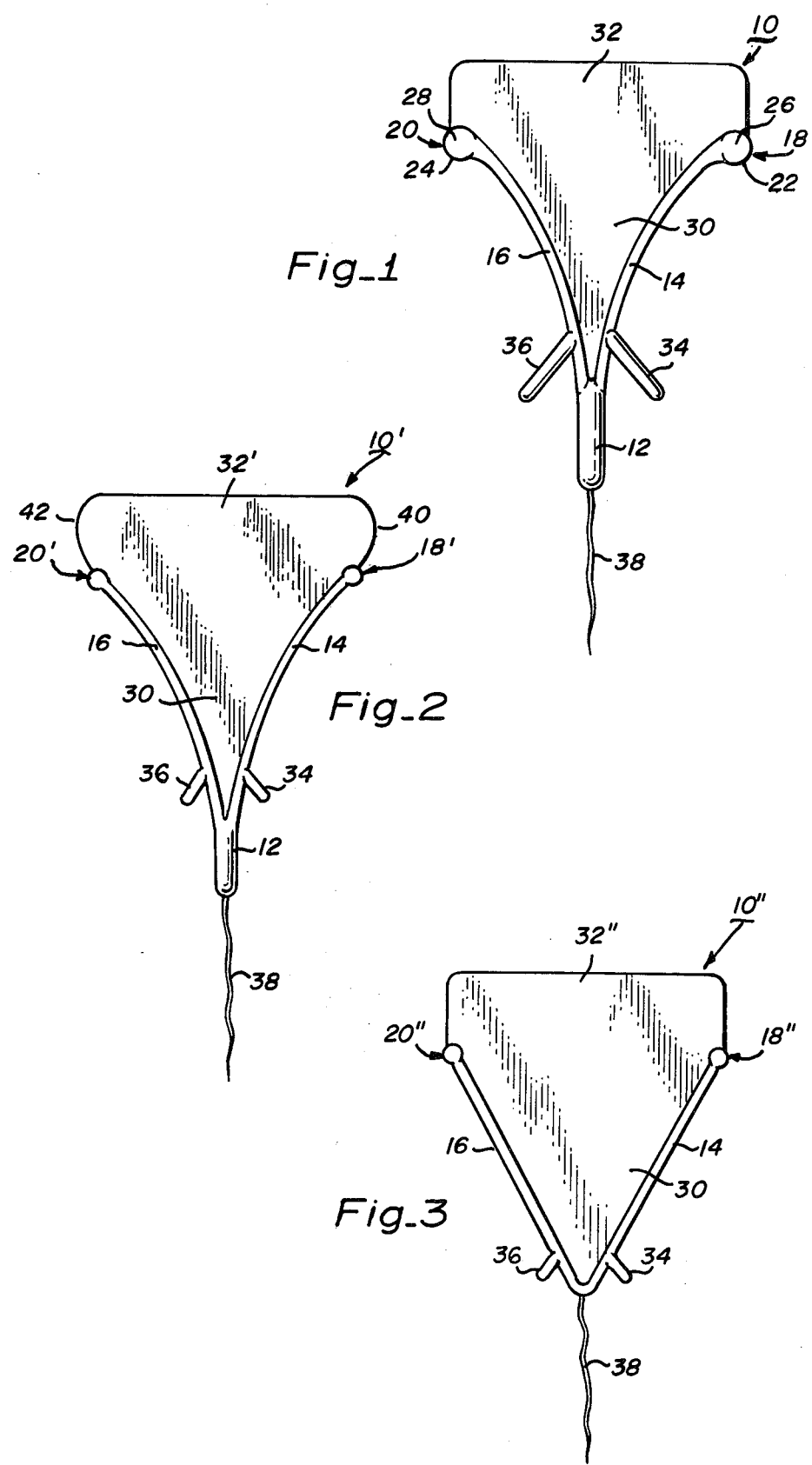

INTRAUTERINE DEVICE

This application is a division of application Ser. No. 549,584, filed Feb. 13, 1975, now U.S. Pat. No. 4,038,978.

FIELD OF THE INVENTION

This invention relates to intrauterine contraceptive devices. More particularly, this invention relates to Y- or V-shaped intrauterine devices of the type generally described in U.S. Pat. Nos. 3,507,274 and 3,811,435. Related intrauterine devices are also described in U.S. Pat. Nos. 3,253,590, 3,633,574, and 3,645,258.

SUMMARY OF THE INVENTION

The intrauterine device of this invention includes a resilient Y- or V-shaped member having two arms gradually and continuously diverging upwardly and outwardly from the intersection thereof adjacent the base portion of the resilient member. The arms are sufficiently resilient so they can be urged together when the intrauterine device is drawn into an inserter prior to insertion of the intrauterine device into the uterus. Upon insertion into the uterus, the arms, due to the resilient nature thereof, return to their original uncompressed shape. In this condition, the outer surfaces thereof contact the adjacent sidewalls of the uterus in such a manner that the device is desirably retained within the uterus. If the resilient member is not plastic, it is preferably encased in a plastic or rubber material, such as, for example, medical grade or clean grade silicone rubber. A thin flexible membrane or web extends between the two diverging arms and covers not only the entire area between the arms but extends above them in a generally rectangular fashion, although other shapes and configurations are contemplated as being within the scope of this invention. The function of the membrane is to contact all or substantially all of the surface area of the uterus thereby preventing nidation or implantation of a fertilized ovum. In addition, the higher membrane enables the intrauterine device to be tailored (i.e., as by cutting) to the exact size of the uterus, thereby substantially eliminating areas of the uterus not adjacent to the intrauterine device where implantation can occur. Optionally, rather than cutting the membrane prior to insertion, the membrane is made of material which is sufficiently flexible such that, if it reaches the fundus upon insertion, it will fold back upon itself and thus completely fill the uterus, once again eliminating areas for implantation of a fertilized ovum. The membrane, extending as it does above the ends of the arms, enables the intrauterine device of this invention to be utilized with both larger and smaller uteri, thus obviating the need to manufacture devices of different size and shape.

Adjacent to the intersection at the base portion of the device, there may be a pair or plurality of flexible spurs or protuberances extending from the arms which are intended to assist in preventing expulsion of the device once it is in position within the uterus. Unlike the spurs on certain known, commercially-available devices which are rigid, the spurs contemplated hereby are soft and flexible so as not to penetrate the endometrial lining of the uterus.

A flexible tail or monofilament string is connected to the intersection at the base portion of the device and is grasped when it is desired to remove the device from the uterus. A monofilament string is preferably utilized since such a string is of substantially smaller dimension than the flexible tail shown, for example, in U.S. Pat. Nos. 3,507,274 and 3,811,435 and, accordingly, will cause less irritation when in position in the cervical os, offer less surface area for growth of infection-causing microorganisms and will cause less dilation of the upper endocervical canal thereby reducing partial expulsion of the device. In addition, with devices having a flexible tail, it is necessary to push the intrauterine device into the inserter (see, for example, FIG. 1 of U.S. Pat. No. 3,507,274 and FIGS. 1, 3 and 5 of U.S. Pat. No. 3,811,435). With a monofilament string, the intrauterine device is pulled into the inserter by pulling on the string after it is threaded through the hollow plunger of the inserter. This technique obviates the need for sterile gloves which can be a problem in remote areas of underdeveloped countries.

In one embodiment, the intrauterine device of this invention includes a resilient Y- or V-shaped member having two arms gradually and continuously diverging upwardly and outwardly from the intersection thereof adjacent the base portion of the resilient member, each of the arms being, at the uppermost portion thereof, curved outwardly, downwardly, and inwardly to form a bent-back portion in the form of a partial loop terminating short of contacting the body of the adjacent arm. The resilient member is totally encased in a plastic or rubber material, preferably, silicone rubber, the encasement about each of the partial loops being in the form of a bead having a flat surface parallel to a plane passing through the resilient member and a curved outside surface along the bent-back portion, the curved outside surface being adapted to contact the adjacent side wall of the uterus when the intrauterine device is in position within the uterus.

In a further embodiment, the intrauterine device of this invention includes a resilient Y- or V-shaped member having two arms gradually and continually diverging upwardly and outwardly from the intersection thereof adjacent the base portion of the resilient member, each of the arms terminating, at the uppermost portion thereof, in a relatively bulbous end portion. Each bulbous end portion has a flat surface parallel to a plane passing through the resilient member and curved side surface adapted to contact the adjacent sidewall of the uterus when the intrauterine device is in position within the uterus, such contact during use being due to the resilient nature of the arms.

The bulbous end portions or beads should be sufficiently small so as not to render insertion of the device unusually painful. If desired, the bulbous end portions or beads can be eliminated; however, they do provide curved, smooth surfaces for contact of the device with the adjacent sidewalls of the uterus and, thereby do serve a beneficial function.

BRIEF DESCRIPTION OF THE DRAWING

FIGS. 1, 2 and 3 are diagrammatic side elevations of intrauterine devices embodying the invention.

Referring to FIG. 1, there is shown an intrauterine device 10 having a base or intersection 12 and a pair of arms 14 and 16 divering upwardly and outwardly therefrom. As shown in U.S. Pat. Nos. 3,507,274 and 3,811,435, the entire disclosures of which are incorporated herein by reference, the device comprises a resilient Y- or V-shaped resilient member totally encased within a plastic or rubber material, preferably clean-grade or medical-grade silicone rubber. Beads 18 and 20 at the ends of arms 14 and 16, respectively, have curved side surfaces 22 and 24, respectively, which are adapted to contact the adjacent sidewalls of the uterus when the intrauterine device is in position therein. Between arms 14 and 16 there is a membrane 30 having a portion thereof 32 which extends, in rectangular fashion, above an imaginary line passing through the ends of arms 14 and 16. As set forth above, it is the function of the membrane to contact the adjacent flat surfaces of the uterus and thereby prevent nidation or implantation of a fertilized ovum. Portion 32 permits the use of a single device for both nulliparous and multiparous women since the device can be tailored (if desired) to fit uteri of varying lengths. After determining the length of the uterus prior to insertion of the device, portion 32 of membrane 30 can be suitably cut to provide an intrauterine device of the desired length. Optionally, since the membrane is so thin as to be extremely flexible, the device can be used as is, in which case membrane portion 32 will naturally fold back upon itself (i.e., toward intersection 12) as it comes into contact with the fundus upon insertion. The device, therefore, is readily adaptable for smaller-sized uteri. Adjacent to intersection 12 there are flexible spurs or protuberance 34 and 36 adapted tp prevent expulsion of the device from the uterus. These spurs are optional and can be eliminated if desired. Connected to intersection 12 is a string or tell-tale 38 which extends through the cervical os and is used to remove the device from the uterus when desired. Since string 38 is of significantly smaller dimension than the flexible tail of U.S. Pat. Nos. 3,507,274 and 3,811,435, it permits easier insertion of the intrauterine device into the inserter therefor and, in addition, affords less chance for infection or expulsion when the intrauterine device is in position within the uterus.

In FIGS. 2 and 3, like numerals are utilized to designate elements common with the device of FIG. 1. Referring to FIG. 2, it can be seen that beads 18' and 20' are of substantially smaller dimension than the corresponding beads of the device of FIG. 1. In addition, portion 32' of membrane 30 has slightly rounded side portions 40 and 42 which are intended to cover those portions of the uterus adjacent to the entrance of the fallopian tubes into the uterus. Referring to FIG. 3, it can be seen that the intrauterine device shown therein is of generally V-shape and is adapted to contact a greater proportion of the uterine walls. The device is also devoid of intersection 12 which, as set forth above, reduces dilation of the upper endocervical canal, thereby minimizing partial expulsion of the device through the cervix. As with the device of FIG. 2, beads 18" and 20" are of smaller dimension than the corresponding beads of the device of FIG. 1. These will provide the curved, smooth surfaces for contacting the adjacent sidewalls of the uterus, but will be less painful to the patient (than the beads of the device of FIG. 1) upon insertion of the device through the cervix.

In the devices above, web portion 32 (or 32' or 32") extends about 0.5 to about 1 cm. above the terminal ends of arms 14 and 16. This extension provides sufficient length to achieve the advantages set forth above.

In a further modification, one of arms 14 and 16 can be of slightly shorter length than the other arm so, when the device is positioned within the inserter, the beads or bulbous end portions are aligned, one below the other, in essentially linear fashion. This minimizes the size and dimension of the leading edge of the device thereby reducing patient discomfort upon insertion.

While the present invention has been described with reference to a specific embodiment thereof, it will be understood by those skilled in this art that various changes may be made and equivalents may be substituted without departing from the true spirit and scope of the invention. For example. the Y- or V-shaped member can be made of polyethylene or nylon, if desired, provided the material has the desired resiliency over the anticipated period of use; the device can be used to carry a progestogen (e.g., progesterone), elemental copper, zinc or a soluble nontoxic compound thereof, or other drug (e.g., an antigonadotrophin) to the uterine cavity to further enhance the contraceptive effect thereof, etc. Additionally, modifications may be made to adapt a particular situation, material, structural desirability or then-present objective to the spirit of this invention without departing from its essential teachings.

What is claimed is:

1. An intrauterine device comprising a resilient Y- or V-shaped member, said resilient member having two arms gradually and continuously diverging upwardly and outwardly from the intersection thereof adjacent the base portion of said resilient member; said arms being sufficiently resilient so said arms can be urged together during positioning of said intrauterine device in an inserter for inserting said intrauterine device into a uterus; a unitary flexible membrane extending between said arms, said membrane covering the entire area between said arms and extending above an imaginary line passing through the end of said arms a dimension sufficient to contact the fundus of a uterus, the extending portion of said membrane terminating in a substantially linear edge and covering a substantially rectangular area defined by said end portions and said substantially linear edge and a flexible string attached to said intersection, said string being adapted to extend outwardly through the cervix when said intrauterine device is in position within the uterus.

2. The intrauterine device of claim 1 wherein said resilient member comprises stainless steel wire encased in a plastic or rubber material.

3. The intrauterine device of claim 2 wherein said plastic rubber material comprises medical grade silicone rubber.

4. The device of claim 1 further including a plurality of flexible spurs attached to said arms, said spurs adapted to prevent the expulsion of said intrauterine device when said intrauterine device is positioned within the uterus.

5. The device of claim 1 wherein said resilient member is encased in a medical grade or clean grade plastic or rubber material.

* * * * *

UNITED STATES PATENT AND TRADEMARK OFFICE
CERTIFICATE OF CORRECTION

PATENT NO. : 4,117,839
DATED : October 3, 1978
INVENTOR(S) : John McLean Morris

It is certified that error appears in the above-identified patent and that said Letters Patent are hereby corrected as shown below:

In the Abstract, line 3, after "Y-", delete "and".

Column 3, line 26, change "protuberance" to --protuberances--.

Column 3, last line, after "0.5" insert --cm--.

Column 4, line 12 of claim 1, insert ";" after --arms--.

Column 4, line 2 of claim 3, after "plastic" insert --or--.

Signed and Sealed this

Nineteenth Day of December 1978

[SEAL]

Attest:

RUTH C. MASON
Attesting Officer

DONALD W. BANNER
Commissioner of Patents and Trademarks